United States Patent
Miyamoto et al.

(10) Patent No.: US 6,171,599 B1
(45) Date of Patent: Jan. 9, 2001

(54) PROCESS FOR PRODUCING EFONIDIPINE HYDROCHLORIDE PREPARATIONS

(75) Inventors: Misao Miyamoto; Toshihisa Oda; Toyohiko Bunrin, all of Funabashi; Toshio Okabe; Tetsuyuki Nishiyama, both of Saitama-ken, all of (JP)

(73) Assignees: Nissan Chemical Industries, Ltd.; Zeria Pharmaceutical Co., Ltd., both of Tokyo (JP)

( * ) Notice: Under 35 U.S.C. 154(b), the term of this patent shall be extended for 0 days.

(21) Appl. No.: 09/142,208

(22) PCT Filed: Mar. 17, 1997

(86) PCT No.: PCT/JP97/00842

§ 371 Date: Sep. 9, 1998

§ 102(e) Date: Sep. 9, 1998

(87) PCT Pub. No.: WO97/34610

PCT Pub. Date: Sep. 25, 1997

(30) Foreign Application Priority Data

Mar. 18, 1996 (JP) .................................................. 8-088868
Mar. 18, 1996 (JP) .................................................. 8-088869

(51) Int. Cl.[7] .............................. A61K 9/00; A61K 9/14; A61K 31/66; A01N 57/36
(52) U.S. Cl. .......................... 424/400; 424/489; 514/110
(58) Field of Search .................................. 424/400, 489; 514/110

(56) References Cited

U.S. PATENT DOCUMENTS 4,983,593 * 1/1991 Miyajima et al. .................... 514/110

FOREIGN PATENT DOCUMENTS 0 230 944   8/1987 (EP) .
0 344 603 A1 12/1989 (EP) .
2-49728    2/1990 (JP) .

* cited by examiner

Primary Examiner—Gollamudi S. Kishore
Assistant Examiner—Todd D Ware
(74) Attorney, Agent, or Firm—Oliff & Berridge, PLC

(57) ABSTRACT

An amorphous solid dispersion of efonidipine hydrochloride having a high intestinal absorbability can be formed by subjecting a mixture containing efonidipine hydrochloride of the formula (I), hydroxypropylmethylcellulose acetate succinate and optionally a thermostabilizer to a step A of heat treatment at from 85 to 140° C. or mechanochemical treatment at from 0 to 140° C., and then to a step B of dipping treatment into a water-containing solution, impregnation treatment with a water-containing solution or contacting treatment with a water vapor-containing gas; or treating the above-mentioned mixture with a hot steam at from 100 to 140° C. and a high pressure. Further, in the above-mentioned step A, the mixture is subjected to high frequency heating, making it possible to give a solid dispersion of efonidipine hydrochloride having a high intestinal absorbability without using the step B. This process is quite advantageous in the production in that the use of an organic solvent is not required. Formula (I):

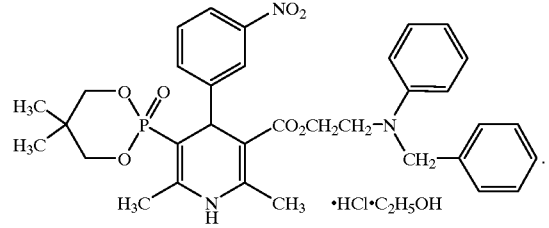

4 Claims, No Drawings

PROCESS FOR PRODUCING EFONIDIPINE HYDROCHLORIDE PREPARATIONS

TECHNICAL FIELD

The present invention relates to a process for producing a novel solid dispersion of a 1,4-dihydro-2,6-dimethyl-5-(5, 5-dimethyl-2-oxo-1,3,2-dioxaphosphorinan-2-yl)-4-(3-nitrophenyl)-3-pyridinecarboxylic acid 2-[benzyl(phenyl) amino]ethyl ester hydrochloride-ethanol solvate (1:1) (hereinafter referred to as "efonidipine hydrochloride") which has an antihypertensive activity, and to oral preparations containing this solid dispersion.

BACKGROUND ART

Efonidipine hydrochloride which is an active ingredient of a pharmaceutical preparation produced by the present invention is a 1,4-dihydropyridine-5-phosphonic acid derivative of the formula:

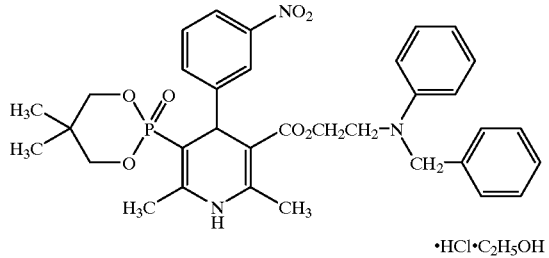

·HCl·$C_2H_5OH$ and it is a compound which is useful as a medication for circulatory organs having a vasodilative activity and an antihypertensive activity owing to a calcium antagonism.

Efonidipine hydrochloride is a slightly-soluble medication, and has, therefore, a poor absorbability. In order to increase the absorbability, there are a method in which particles of an original medication are subjected to supermicro-particle powdering and a wettability or a dispersibility is improved, and a method in which a solubility of an original medication is improved by formation of a solid dispersion. A method in which a solid dispersion is formed by rendering a medication amorphous attracts special attention. The solid dispersion is a substance obtained by dispersing a medication into a carrier in a monomolecular state. In this dispersion, the medication is retained in a completely amorphous state. In general, an amorphous form is, compared to a crystal form, in a high energy state, and is therefore expected to have a high absorbability.

In a method of producing a solid dispersion of efonidipine hydrochloride, it is known that efonidipine hydrochloride and hydroxypropylmethylcellulose acetate succinate (hereinafter referred to as "HPMC-AS") is dissolved in an organic solvent, and the solvent is removed from the resulting solution through drying under reduced pressure, spray-drying, freeze-drying or the like to form a powdery or particulate product, or the solution is spray-coated on a particulate pharmaceutical excipient as a core through fluidized bed coating, centrifugal fluidized bed coating, pan coating or the like, or the solution is added to a pharmaceutical excipient, and the mixture is kneaded, then dried and formed into a granular product [Japanese Patent Application Laid-open No. Hei 2-49728 (49728/1990), U.S. Pat. No. 4,983,593 and European Patent No. 344,6031].

The method described in these references is excellent as a method of improving a solubility and an absorbability of efonidipine hydrochloride. However, it was problematic in that since a large amount of an organic solvent is used, the production cost is high, and the solvent sometimes remains in the medication.

DISCLOSURE OF INVENTION

The present inventors have assiduously conducted investigations to overcome the problems involved in this conventional method, and have consequently found a process for producing a solid dispersion containing efonidipine hydrochloride, which comprises subjecting a mixture of efonidipine hydrochloride and HPMC-AS to a step A of heat treatment at from 85 to 140° C. or mechanochemical treatment at from 0 to 140° C., and then to a step B of dipping treatment into a water-containing solution, impregnation treatment with a water-containing solution or contacting treatment with a water vapor-containing gas; or treating the above-mentioned mixture with a hot steam at from 100 to 140° C. and a high pressure.

Further, the present inventors have found a process for producing a solid dispersion in which in the heat treatment in the step A, the mixture of efonidipine hydrochloride and HPMC-AS is subjected to high frequency heating at from 80 to 160° C. without the need of the step B.

The heat treatment in the step A is conducted in the temperature range of which the upper limit is a temperature at which efonidipine hydrochloride is not deteriorated by decomposition. Such a temperature is, for example, between 85° C. and 140° C., preferably between 85° C. and 120° C., more preferably between 90° C. and 120° C. The heat treatment time is between 20 minutes and 120 minutes, preferably between 20 minutes and 90 minutes. Further, the heating can be conducted at from 85° C. to 160° C. by adding a thermostabilizer to the above-mentioned mixture.

The heating can be conducted not only through ordinary hot-plate heating or steam heating but also through infrared heating or far infrared heating.

When high frequency heating is employed as heat treatment in the step A, it is conducted at, for example, from 80° C. to 160° C., preferably at from 80° C. to 140° C., more preferably at from 90° C. to 130° C. for from 1 minute to 60 minutes, preferably for from 5 minutes to 20 minutes. Further, the heating can be conducted at from 80° C. to 180° C. by adding a thermostabilizer to the above-mentioned mixture.

The mechanochemical treatment is conducted in the temperature range of which the upper limit is a temperature at which efonidipine hydrochloride is not deteriorated by decomposition. Such a temperature is, for example, between 0° C. and 140° C., preferably between 0° C. and 80° C., more preferably between 15° C. and 60° C. The mechanical energy treatment under the same energy conditions as the above-mentioned heat treatment is conducted usually for from 1 minute to 120 minutes, preferably for from 3 minutes to 90 minutes in view of the quality control, the uniformity and the energy saving. In this mechanochemical treatment, care must be taken to avoid the local increase in the temperature. Further, the heating from outside is not particularly required. Still further, the treatment can be conducted at from 0° C. to 160° C. by adding a thermostabilizer.

A solid dispersion having not only an improved wettability of the surface of the solid dispersion but also a superior absorbability can be formed by dipping treatment into a water-containing solution, impregnation treatment with a water-containing solution or contacting treatment with a water vapor-containing gas in the step B. This method can increase the molecular motion between the amorphous substance of efonidipine hydrochloride and HPMC-AS, making it possible to increase a micro-dispersion and to delocalize the localized amorphous substance of efonidipine hydrochloride.

The water-containing solution which is used in the above-mentioned method is water per se or an aqueous solution of an inorganic material, a surfactant or an organic solvent such as ethanol or the like. The water vapor-containing gas refers to a water vapor containing a vapor of an organic solvent such as ethanol or the like, air, oxygen, hydrogen and/or nitrogen.

Instead of the two-step treatment, namely, the step A including the heat treatment or the mechanochemical treatment for conversion to an amorphous state and then the step B including the dipping treatment into the water-containing solution, the impregnation treatment with the water-containing solution or the contacting treatment with the water vapor-containing gas, the step A of conversion to the amorphous state and the step B of the micro-dispersion can also be conducted at the same time by treating a mixture of efonidipine hydrochloride and HPMC-AS with a hot steam at from 100 to 140° C. and high pressure.

Meanwhile, in the case of the high frequency heating in the step A, the high frequency directly vibrates the water molecule to delocalize the localized amorphous substance of efonidipine hydrochloride and increase the micro-dispersion simultaneously with the conversion of efonidipine hydrochloride to the amorphous state through the heat treatment, whereby the stability and the absorbability of the amorphous substance can be increased without using the step B.

In the production of the solid dispersion, the stability can be further increased by adding a thermostabilizer. Further, oral preparations of efonidipine hydrochloride can be produced upon using the solid dispersion of the present invention.

HPMC-AS which is used in the present invention is a mixed ester of hydroxypropylmethylcellulose with acetic acid and a monosuccinic acid. SHIN-ETSU AQOAT (trade name for a product of The Shin-etsu Chemical Co., Ltd.) is taken as an example.

The composition of a substituent of HPMC-AS used in the present invention is preferably between 0.1 and 0.4 in terms of an average value (succinoyl DS value) of the number of a hydroxyl group with which a succinyl group is substituted for one glucose residue of acellulose.

The preferable results are provided by containing HMPC-AS in an amount of from 1 to 7 parts by weight, especially from 3 to 5 parts by weight per part by weight of efonidipine hydrochloride.

The thermostabilizer in the present invention is an additive which can prevent efonidipine hyrochloride or HPMC-AS from being deteriorated by decomposition through the heating or the mechanochemical treatment. Examples of the thermostabilizer include phospholipids such as lecithin and cephalin; phenol compounds such as guaiacum, nordihydroguaiaretic acid, dibutylhydroxytoluene, butylhydroxyanisole and propyl gallate; quinone compounds such as hydroquinone; tocopherols; alkanolamine; sorbitol; glycerin; adipic acid; citric acid; ascorbic acid; phosphoric acid; urea; sodium sulfite; sodium hydrosulfite; amino acids; aminoethylsulfonic acid; glycyrrhizinic acid; tartaric acid; succinic acid; fumaric acid; inacrogol; maltose; maltol; mannitol; and meglumine.

Preferable themostabilizers are phospholipids, propyl gallate, tocopherol, ascorbic acid, urea, amino acids, glycyrrhetinic acid, tartaric acid, succinic acid, maltol and mannitol.

More preferable is urea.

The amount of the thermostabilizer used in the present invention is between 0.1 and 3 parts by weight, preferably between 0.3 and 1.5 parts by weight, more preferably between 0.3 and 1 part by weight per part by weight of efonidipine hydrochloride, whereby the excellent results are provided.

The process for producing the solid dispersion containing efonidipine hydrochloride in the present invention is described in detail below.

Step A

The amorphous substance which is a precursor of the solid dispersion in the present invention is formed by subjecting a mixture of efonidipine hydrochloride and HMPC-AS, preferably a mixture of efonidipine hydrochloride, HMPC-AS and a thermostabilizer to wet granulation or roller compacted granulation (mixing) and heat-treating the mixture either simultaneously with or after the granulation, or to mechanochemical treatment under the same energy conditions as the heat treatment.

The granulation (mixing) is conducted in a usual manner, for example, using a universal mixer, a fluidized bed granulation machine, a dash mill, a wet granulation machine, a roller compacted granulation machine or the like. The resulting granules are easily milled, and the diameter of the granules is usually between 0.05 mm and 3 mm. The heat treatment may be conducted at the time of the granulation as mentioned above. Further, the heat treatment may be conducted, after the granulation, in a hot air dryer, a flow dryer, a gyrodryer, a powder dryer or the like.

The heating can be conducted not only through usual hot plate heating or steam heating but also through infrared heating or far infrared heating.

The heat treatment by which to convert a crystalline state of efonidipine hydrochloride to an amorphous state is conducted in the temperature range of which the upper limit is a temperature at which efonidipine hydrochloride is not deteriorated by decomposition. Such a temperature is, for example, between 85° C. and 140° C., preferably between 85° C. and 120° C., more preferably between 90° C. and 120° C. The heat treatment time is between 20 minutes and 120 minutes, preferably between 20 minutes and 90 minutes. Further, the addition of the thermostabilizer can prevent efonidipine hydrochloride or HPMC-AS to be deteriorated by decomposition. Thus, it is possible to conduct the treatment in a wider temperature range, for example, at from 85° C. to 160° C.

When the high frequency heating is conducted as the heat treatment, the temperature is, for example, between 80° C. and 160° C., preferably between 80° C. and 140° C., more preferably between 90° C. and 130° C. The heat treatment time is between 1 minute and 60 minutes, preferably between 5 minutes and 20 minutes. Further, the heating can be conducted at from 80° C. to 180° C. by adding the thermostabilizer to the above-identified mixture.

The conversion to the amorphous state can be conducted also by the mechanochemical treatment with not only the heat in the heat treatment, but also a mechanical energy of compression, shearing, friction or the like as an energy to be added. For example, the conversion to the amorphous state can also be conducted, without heating the above-mentioned essential components, only through the mechanochemical treatment such as pulverization with a ball mill, treatment with a planetary mill, treatment with a compression press, treatment with a shear roll, treatment with a kneader or the like. This method makes it easy to control formation of thermal decomposed substances.

The mechanochemical treatment is conducted in the temperature range of which the upper limit is a temperature at which efonidipine hydrochloride is not deteriorated by decomposition. Such a temperature is, for example, between 0° C. and 140° C., preferably between 0° C. and 80° C., more preferably between 15° C. and 60° C. The mechanical energy treatment under the same energy conditions as the above-mentioned heat treatment is conducted usually for from 1 minute to 120 minutes, preferably for from 3 minutes to 90 minutes in view of the quality control, the uniformity and the energy saving. In this mechanochemical treatment, care must be taken to avoid the local increase in the temperature. Further, the heating from outside is not particularly required. Still further, the addition of the thermostabilizer helps to prevent efonidipine hydrochloride or HPMC-PAS from being deteriorated by decomposition, and enables the treatment in a wider temperature range of, for example, from 0° C. to 160° C.

Further, the heat treatment and the mechanochemical treatment can be conducted also in combination.

Step B

In order to further increase the absorbability of the thus-formed amorphous substance of efonidipine hydrochloride from the intestines, it is advisable that the resulting amorphous substance be dipped in a water-containing solution either as such or after being milled, or be impregnated with a water-containing solution, or be brought into contact with a water vapor-containing gas, and be dried as required.

The solid dispersion which has not only the improved wettability of the surface of the solid dispersion but also the superior absorbability can be produced by the dipping treatment into the water-containing solution, the impregnation treatment with the water-containing solution or the contacting treatment with the water vapor-containing gas. This is because the above-mentioned method increases the molecular motion between the amorphous substance of efonidipine hydrochloride and the amorphous stabilizer, making it possible to enhance the micro-dispersion and to delocalize the localized amorphous substance of efonidipine hydrochloride.

The water-containing solution used in the above-mentioned method refers to water per se or an aqueous solution of an inorganic substance, a surfactant or an organic solvent such as ethanol or the like. The water vapor-containing gas refers to a water vapor containing a vapor of an organic solvent such as ethanol or the like, air, oxygen, hydrogen and/or nitrogen.

The necessary amount of the water-containing solution is between 0.1 and 5 parts by weight, preferably between 0.3 and 3 parts by weight per part by weight of efonidipine hydrochloride.

In the case of the water vapor-containing gas, the treatment at a high pressure is possible. However, the contacting treatment is usually conducted at normal pressure from the surface of the device. In the contacting treatment, the temperature is between 40° C. and 95° C., the relative humidity is preferably between 50 and 100%, and the contacting time is preferably between 30 minutes and 120 minutes.

In the drying which is conducted as required after increasing the micro-dispersion, the drying temperature is between 60° C. and 110° C., especially preferable between 70° C. and 90° C., and the drying time is between 15 minutes and 180 minutes, especially preferably between 30 minutes and 90 minutes. It is also possible that the solid dispersion is directly formed without conducting the drying.

Instead of the two-step treatment, namely, the step A including the heat treatment or the mechanochemical treatment for the conversion to the amorphous state and then the step B including the dipping treatment into the water-containing solution, the impregnation treatment with the water-containing solution or the contacting treatment with the water vapor-containing gas for the micro-dispersion, the step A for the conversion to the amorphous state and the step B for the micro-dispersion can also be conducted at the same time by treating the substance with a hot steam at high pressure.

The treatment with the hot steam at the high pressure means that the substance is allowed to stand in a high-temperature and high-pressure steam of at least 100° C. and at least 1 atm. using a pressure container such as an autoclave, a steam sterilizer or the like.

The temperature is between 100° C. and 140° C., and the pressure at this time is between 1 and 3.7 kg/cm$^2$. Preferably, the temperature is between 100° C. and 120° C., and the pressure is between 1 and 2 kg/cm$^2$.

With respect to the heating in the step A, not only the ordinary heating but also the high frequency heating can be used. The high frequency heating includes high frequency dielectric heating, high frequency induction heating and plasma heating. The high frequency dielectric heating is especially preferable.

The frequency zone can be selected depending on a substance to be heated. Microwave heating using a microwave zone is especially preferable. Four frequencies which are distributed as ISM (Industrial, Scientific and Medical) frequencies under the Wireless Telegraphy Act, namely, 915, 2450, 5800 and 22125 MHz can be used as the frequency in the microwave heating. Generally, the frequency, 915 or 2450 MHz can be used.

The microwave heating can be conducted using an oven system (electronic oven system or conveyor system) or a wave guide system depending on a shape of a substance to be heated.

The conveyor system is a device in which a mixture can be mounted on a belt and continuously heated by being passed through a layer which has been irradiated with a microwave. It is appropriate for mass production. There is, for example, a continuous microwave heater of Micro Denshi Co. Ltd.

In the high frequency heating, the heating temperature of the substance to be heated can be controlled with the high frequency output, the treatment time or the thickness of the substance to be heated, or by adding water to the substance to be heated at the time of the heating. Further, in the microwave heating with the conveyor system, it can be controlled by the feed rate of the belt. The feed rate is between 0.1 and 500 cm/min, especially preferably between 2 and 50 cm/minute.

The controlling can easily be conducted by optimizing the amount of water added. The amount of water added, for example, in the heating with the frequency of 2450 MHz, is between 0.1 and 10 parts by weight, preferably between 0.3 and 5 parts by weight, more preferably between 0.5 and 3 parts by weight per part by weight of efonidipine hydrochloride.

The solid dispersion obtained by the high frequency heating in the step A, even if the step B is not conducted, exhibits the same absorbability as the solid dispersion obtained through the step A of the usual heat treatment or mechanochemical treatment and the subsequent step B or through the treatment with the hot steam at high pressure.

The conversion to the amorphous state in the present invention can be conducted also by incorporating a surfactant, an antiseptic and the like as components other than the essential components. The incorporation of one or more types of the thermostabilizer can allow the conversion to the amorphous state.

The solid dispersion of efonidipine hydrochloride obtained by the conversion to the amorphous state in the present invention is sprayed with water, a surfactant aqueous solution or an organic solvent such as ethanol or the like, or treated therewith in solution either as such or after being milled, and is then redried, making it possible to improve the surface properties and the wettability of the solid dispersion.

In the process for producing the solid dispersion obtained by the method of conversion to the amorphous state and the oral administrations containing the solid dispersion in the present invention, it is possible to add a pharmaceutical excipient (for example, crystalline cellulose and lactose), a disintegrant, a lubricant and/or a colorant which are generally known in the field of preparations, as required.

The oral administrations include capsules, granules, pills, fine granules, powders, tablets, troches and sublingual tablets.

In these oral administrations, efonidipine hydrochloride of the present invention is contained at a dose of from 5 to 80 mg per day.

BEST MODE FOR CARRYING OUT THE INVENTION

The necessity of the essential components and the process in the present invention are illustrated specifically by referring to the following Examples.

Test Method

The powder X-ray diffractometry of efonidipine hydrochloride was conducted, and the diffraction angle 2θ and the strength before and after conversion to the amorphous state were plotted. Approximation was conducted through a regression straight line, and the slope was defined as a degree of crystallinity.

EXAMPLE 1

Sixty grams of efonidipine hydrochloride, 180 g of HPMC-AS, 30 g of urea and 30 g of water were mixed, and the mixture was subjected to wet granulation using a universal mixer. The resulting wet granules were heated at 120° C. for 1 hour using a hot air dryer, and further brought into contact with a steam for 40 minutes in a constant temperature and humidity chamber of 80° C. and 90-% RH to obtain a solid dispersion. This solid dispersion was identified to be an amorphous substance through powder X-ray diffractometry. Crystalline cellulose or the like was added to this solid dispersion. The mixture was subjected to roller compacted granulation in a usual manner. The granules were formed into a solid tablet containing 20 mg of efonidipine hydrochloride. The absorbability of this solid tablet in a dog was excellent.

EXAMPLE 2

Sixty grams of efonidipine hydrochloride, 180 g of HPMC-AS and 30 g of water were mixed, and the mixture was subjected to wet granulation using a universal mixer. The resulting wet granules were heated at 95° C. for 2 hours using a hot air dryer, and further brought into contact with a steam for 60 minutes in a constant temperature and humidity chamber of 85° C. and 90-% RH to obtain a solid dispersion. This solid dispersion was identified to be the same amorphous substance as that obtained in Example 1 through the powder X-ray diffractometry.

EXAMPLE 3

A mixture of 3 g of efonidipine hydrochloride, 6 g of HPMC-AS and 1.5 g of urea was subjected to mechanochemical treatment at room temperature (from 15 to 25° C. ) and 100 G for 3 minutes using a high-speed planetary mill, and then milled. Water (1.5 g) was added thereto, and the resulting mixture was heated at 90° C. for 30 minutes to obtain a solid dispersion. The powder X-ray diffractometry of this solid dispersion was conducted. Consequently, no crystal peak was identified.

EXAMPLE 4

Sixty grams of efonidipine hydrochloride, 180 g of HPMC-AS, 30 g of urea and 30 g of water were mixed, and the mixture was subjected to wet granulation using a universal mixer. The wet granules were subjected to the microwave heating for 4 minutes using a microwave heater (2450 MHz, 500 W) to obtain a solid dispersion. At that time, the final temperature was 130° C.

The powder X-ray diffractometry of this solid dispersion was conducted. Consequently, no crystal peak was identified.

Comparative Example 1

A solid dispersion was produced in exactly the same manner as in Example 1 except that the heat treatment using the hot air dryer was conducted at 80° C. for 1 hour. The degree of crystallinity of this solid dispersion was 70%, and the conversion to the amorphous state was insufficient.

Comparative Example 2

A solid dispersion was produced in exactly the same manner as in Example 1 except that the contacting with a steam for 40 minutes in a constant temperature and humidity chamber of 80° C. and 90-% RH was not conducted. Then, a solid tablet was obtained.

The solid dispersion was identified to be amorphous through the powder X-ray diffractometry. However, the absorbability of this solid dispersion in a dog was approximately ⅓ of that in Example 1 in terms of AUC [area under the (plasma level-time) curve].

EXAMPLE 5

An efonidipine hydrochloride-containing solid dispersion obtained under the same conditions as in Example 1 was milled, screened through a 60-mesh sieve, mixed with lactose and corn starch which had been screened through a 60-mesh sieve, and screened through a 40-mesh sieve to give a powder containing efonidipine hydrochloride in an amount of 40 mg per gram of the powder.

EXAMPLE 6

Sixty grams of efonidipine hydrochloride, 180 g of HPMC-AS, 30 g of urea and 30 g of water were mixed, and the mixture was subjected to wet granulation using a universal mixer. The resulting wet granules were heated for 3 minutes using a microwave heater (2450 MHz, 1500 W) to give a solid powder. At this time, the final temperature was 130° C. This solid dispersion was identified to be amorphous through the powder X-ray diffractometry.

A solid tablet was obtained from this solid dispersion in a usual manner. This solid tablet was subjected to an absorption test in a dog. Consequently, an absorbability which was practically satisfactory was provided.

EXAMPLE 7

Five grams of efonidipine hydrochloride, 25 g of HPMC-AS and 15 g of water were mixed, and the mixture was subjected to microwave heating for 2 minutes using a microwave heater (2450 MHz, 500 W) to give a solid dispersion. At that time, the final temperature was 80° C. This solid dispersion was identified to be amorphous through the powder X-ray diffractometry.

Comparative Example 3

A solid dispersion was produced in exactly the same manner as in Example 6 except that the heat treatment using the microwave dryer was replaced with the hot-plate heating at 80° C. for 1 hour. The degree of crystallinity of this solid dispersion was 70%, and the conversion to the Amorphous state was insufficient.

EXAMPLE 8

An efonidipine hydrochloride-containing solid dispersion obtained under the same conditions as in Example 6 was milled, screened through a 60-mesh sieve, mixed with lactose and corn starch which had been screened through a 60-mesh sieve, and screened through a 40-mesh sieve to give a powder containing efonidipine hydrochloride in an amount of 40 mg per gram of the powder.

EXAMPLE 9

Four-hundred grams of efonidipine hydrochloride, 1200 g of HPMC-AS, 200 g of urea and 2700 g of water were mixed, and the mixture was subjected to the microwave continuous heating using a microwave continuous heater (manufactured by Micro Denshi Co., Ltd., 2450 MHz, 1500 W, irradiation layer: 150 cm, thickness: 4 mm, width: 8 cm, belt speed: 10 cm/min) to give a solid dispersion. At this time, the final temperature was 102° C. This solid dispersion was identified to be amorphous through the powder X-ray diffractometry.

A solid tablet was obtained from this solid dispersion in a usual manner. This solid tablet was subjected to an absorption test in a dog. Consequently, an absorbability which was practically satisfactory was provided.

Industrial Availability

In accordance with the present invention, an amorphous solid dispersion of efonidipine hydrochloride having a high intestinal absorbability can be formed by subjecting a mixture containing efonidipine hydrochloride, hydroxypropylmethylcellulose acetate succinate and optionally a thermostabilizer to a step A of heat treatment at from 85° C. to 140° C. or mechanochemical treatment at from 0 to 140° C., and then to a step B of dipping treatment into a water-containing solution, impregnation treatment with a water-containing solution or contacting treatment with a water vapor containing gas; or treating the above-mentioned mixture with a hot steam at from 100 to 140° C. and a high pressure. Further, in the above-mentioned step A, the mixture is subjected to high frequency heating, making it possible to give a solid dispersion of efonidipine hydrochloride having a high intestinal absorbability without using the step B. This process is quite advantageous in the production in that the use of an organic solvent is not required.

What is claimed is:

1. A process for producing a solid dispersion containing efonidipine hydrochloride, which comprises subjecting a mixture of efonidipine hydrochloride, hydroxypropylmethylcellulose acetate succinate and a thermostabilizer to a) a step A comprising a heat treatment at from 85 to 160° C. or a mechanochemical treatment at from 0 to 160° C., and then to a step B comprising a dipping treatment into a water-containing solution, an impregnation treatment with a water-containing solution or a contacting treatment with a water vapor-containing gas; or b) a treatment of the mixture with a hot steam at from 100 to 160° C. and high pressure.

2. The process of claim 1, wherein the thermostabilizer is urea.

3. A process for producing a solid dispersion containing 1,4-dihydro-2,6-dimethyl-5-(5,5-dimethyl-2-oxo-1,3,2-dioxaphosphorinan-2-yl)-4-(3-nitrophenyl)-3-pyridinecarboxylic acid 2-{benzyl(phenyl)amino}ethyl ester hydrochloride-ethanol solvate (1:1) (hereinafter referred to as "efonidipine hydrochloride"), which comprises subjecting a mixture of efonidipine hydrochloride and hydroxypropylmethylcellulose acetate succinate to a) a step A comprising a heat treatment at from 85 to 140° C. or a mechanochemical treatment at from 0 to 140° C., and then to a step B comprising a dipping treatment into a water-containing solution, an impregnation treatment with a water-containing solution or a contacting treatment with a water vapor-containing gas; or b) a treatment of the mixture with a hot steam at from 100 to 140° C. and high pressure.

4. An oral preparation containing the solid dispersion of efonidipine hydrochloride which is produced by the process of claim 3.

\* \* \* \* \*